United States Patent
Lemonis et al.

(10) Patent No.: US 10,835,420 B2
(45) Date of Patent: Nov. 17, 2020

(54) CORNEAL MARKS IN VISION CORRECTION SURGERY

(71) Applicant: WAVELIGHT GMBH, Erlangen (DE)

(72) Inventors: Sissimos Lemonis, Erlangen (DE); Joerg Klenke, Nuremberg (DE)

(73) Assignee: Alcon Inc. (CH)

( * ) Notice: Subject to any disclaimer, the term of this patent is extended or adjusted under 35 U.S.C. 154(b) by 5 days.

(21) Appl. No.: 15/033,766

(22) PCT Filed: Aug. 7, 2015

(86) PCT No.: PCT/EP2015/068271
§ 371 (c)(1),
(2) Date: May 2, 2016

(87) PCT Pub. No.: WO2017/025115
PCT Pub. Date: Feb. 16, 2017

(65) Prior Publication Data
US 2018/0200111 A1    Jul. 19, 2018

(51) Int. Cl.
*A61F 9/008* (2006.01)
*A61F 9/009* (2006.01)

(52) U.S. Cl.
CPC ......... *A61F 9/00827* (2013.01); *A61F 9/009* (2013.01); *A61F 9/00825* (2013.01); *A61F 2009/00846* (2013.01); *A61F 2009/00872* (2013.01)

(58) Field of Classification Search
CPC ................ A61F 9/008–2009/00897; A61B 34/00–2034/108
USPC ................... 606/4–6, 10–12; 434/262
See application file for complete search history.

(56) References Cited

U.S. PATENT DOCUMENTS

| | | | |
|---|---|---|---|
| 2010/0324542 A1* | 12/2010 | Kurtz | A61F 9/008 606/6 |
| 2015/0018674 A1* | 1/2015 | Scott | A61F 9/00827 600/427 |
| 2015/0116725 A1* | 4/2015 | Lemonis | A61F 9/00802 356/479 |

FOREIGN PATENT DOCUMENTS

| | | | |
|---|---|---|---|
| JP | 2013529979 A | | 7/2013 |
| WO | 2011094666 A1 | | 8/2011 |
| WO | WO2011094666 A1 | | 8/2011 |
| WO | WO2013156046 | * | 10/2013 |
| WO | 2014172621 A2 | | 10/2014 |
| WO | WO2014172545 A1 | | 10/2014 |
| WO | WO2014172621 A9 | | 2/2015 |

* cited by examiner

*Primary Examiner* — Jonathan T Kuo
(74) *Attorney, Agent, or Firm* — Kenneth D. Bassinger, Esq.

(57) ABSTRACT

The present disclosure relates to systems and methods for marking an undeformed cornea with a mark to allow later detection of a selected location on the cornea after deformation and to systems of methods for performing vision correction surgery based on the mark.

17 Claims, 2 Drawing Sheets

CORNEAL MARKS IN VISION CORRECTION SURGERY

CROSS REFERENCE TO RELATED APPLICATIONS

This application is a section 371 national stage phase of International Application No. PCT/EP2015/068271, filed 7 Aug. 2015, titled "CONEAL MARKS IN VISION CORRECTION SURGERY," which is hereby incorporated by reference in its entirety.

TECHNICAL FIELD

The present disclosure relates to systems and methods for performing vision correction surgery.

BACKGROUND

Various vision correction surgeries are presently available to improve patients' vision. These surgeries include laser-assisted corneal ablation surgeries, which change the refractive properties of the cornea to correct for lens defects within the eye. One common such surgery is known as LASIK (laser-assisted in situ keratomileusis) and is used to correct myopia, astigmatism, or more complex refractive errors. These surgeries also include lenticular removal procedures, which use a different method to change the refractive properties of the cornea to correct for lens defects within the eye. One common such surgery is known as SMILE (small incision lenticule extraction) and may be used to correct many of the refractive errors also correctable by LASIK, such as myopia. Other surgeries may correct corneal defects or other problems. These surgeries may be used alone, but some are also compatible with other vision correction surgeries, such as cataract surgery. For instance, LASIK to correct astigmatism is often combined with cataract surgery.

In all such surgeries it is important to perform the correct procedure at the correct location on the cornea in order to provide optimal visual improvement. However, during many such surgeries the cornea is deformed from its normal shape, making it difficult to perform procedures at optimal locations.

Furthermore, for many such surgeries, there is more than one suitable location for the surgical procedure, but different locations provide different benefits to the patient. Currently, many procedures are performed at only one suitable location, leaving the patient with no choice between the various different benefits.

The present disclosure relates to systems and methods for marking the cornea with a mark to allow later detection of a selected location on the cornea and to systems of methods for performing vision correction surgery based on the mark.

In one embodiment, the disclosure provides a method of performing a vision correction surgery by identifying a selected location on a cornea of an eye, marking the periphery of the cornea with a mark that corresponds to the selected location, deforming the cornea, re-identifying the selected location on the deformed cornea based on the mark, and performing a vision correction surgical procedure to at the selected location while the cornea is deformed.

In more specific embodiments, the selected location is a pupil center of the eye, such as the pupil center of a dilated pupil or an undilated pupil. The selected location may be at a pupil center of the eye at a different dilation than during the surgical procedure.

In another more specific embodiment, the selected location is the corneal vertex.

In more specific embodiments, the mark includes a circle or a plurality of sub-marks including at least three sub-marks.

In another more specific embodiment, the mark is made between 8 mm and 11 mm from the approximate corneal vertex.

In other more specific embodiments, the mark may be made using a femtosecond laser or a ring marker.

In another more specific embodiment, the mark includes a biocompatible dye.

In a more specific embodiment, deforming the cornea includes applanating the cornea.

In another more specific embodiment, re-identifying the selected location on deformed cornea based on the mark includes locating the mark, then determining the selected location with respect to the mark.

In another more specific embodiment, the vision correction surgical procedure includes laser ablating a portion of the cornea in the selected location, such as in a LASIK procedure.

In still another more specific embodiment, the vision correction surgical procedure includes removing a lenticule of cornea at the selected location, such as in a SMILE procedure.

The above more specific embodiments may be combined with one another or with other features described herein unless clearly mutually exclusive. The above methods may be used with the following system.

The disclosure also provides a system for vision correction surgery including an ophthalmic detector operable to identify a selected location on a cornea of an eye, a marker operable to mark the periphery of the cornea with a mark that corresponds to the selected location, a corneal suction or applanation device operable to deform the cornea, a surgical procedure device operable to perform a vision correction surgical procedure at the selected location while the cornea is deformed, and a computer programmed with at least an algorithm to identify the selected location and an algorithm to re-identify the selected location based on the mark, using information provided by the ophthalmic detector.

According to a more specific embodiment, the marker and surgical procedure device are the same device, for instance they may both include a femtosecond laser.

According to another more specific embodiment, the ophthalmic detector may include a sensor able to convert light reflected from the eye to a digital image.

The above more specific embodiments may be combined with one another or with other features described herein unless clearly mutually exclusive. The above system may also be used with the above method.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

The present disclosure relates to systems and methods for marking the cornea of an eye with a mark. The mark allows later detection of a selected location on the cornea, such as the center of the pupil at a given dilation or the corneal vertex, even when the cornea has then been deformed. The disclosure further relates to systems and methods for performing vision correction surgery using the mark. The cornea is deformed during such surgery, but the mark allows the surgery to be performed at the selected location despite the deformation, which typically improves the vision correction once the cornea returns to its undeformed shape. The mark further allows the selected location to be the pupil center at a given dilation, or the corneal vertex. Performing a surgical procedure at the corneal vertex as opposed to the pupil center or at the pupil center at one dilation as opposed to another may provide different vision correction.

In the following description, details are set forth by way of example to facilitate discussion of the disclosed subject matter. It should be apparent to a person of ordinary skill in the field, however, that the disclosed embodiments are exemplary and not exhaustive of all possible embodiments.

Figure 1A:
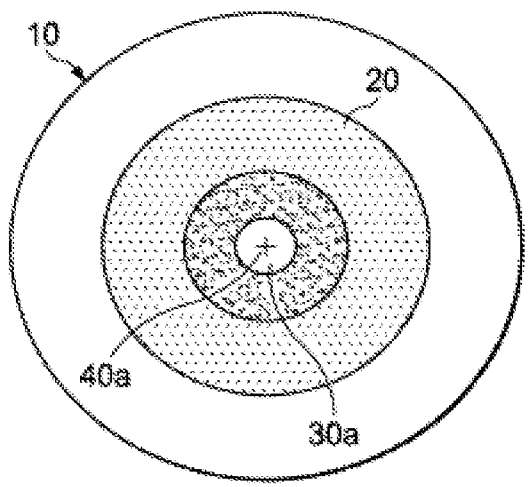
FIG. 1A is a schematic diagram of the pupil center of a highly undilated eye.
Figure 1B:
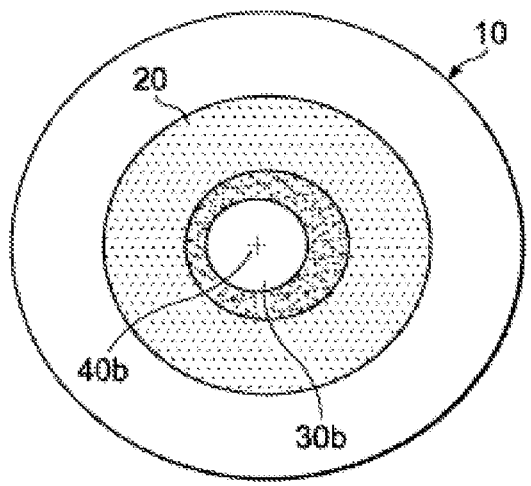
FIG. 1B is a schematic diagram of the pupil center of a highly dilated eye.
Figure 1C:
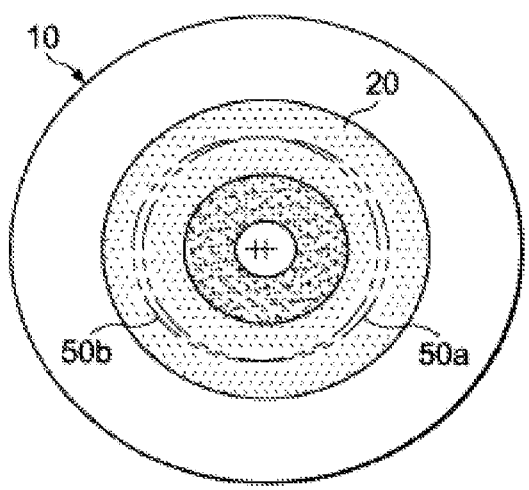
FIG. 1C is a schematic diagram of marks to indicate the pupil centers of the eyes of FIG. 1A and FIG. 1B, according to embodiments of the present disclosure.

Vision correction surgeries are often performed the at the pupil center at whatever dilation occurs during surgery. If pupils were completely symmetrical at all times, the pupil center would remain the same regardless of dilation. However, few pupils are completely symmetrical and, in addition, the asymmetry varies with dilation. As a result, the pupil center also varies with dilation. This can be understood through reference to the diagram of eye 10 with cornea 20 and pupil 30 shown in FIG. 1A and FIG. 1B. Pupil 30a in FIG. 1A is highly undilated and has a pupil center 40a. Pupil 30b in FIG. 1B is highly dilated and has a pupil center 40b, which is not the same location as pupil center 40a. As illustrated in FIG. 1C, mark 50a on the corneal periphery of cornea 20 to indicate undilated pupil center 40a is therefore in a different location than mark 50b made on the corneal periphery of cornea 20 to indicate highly dilated pupil center 40b.

Figure 1D:
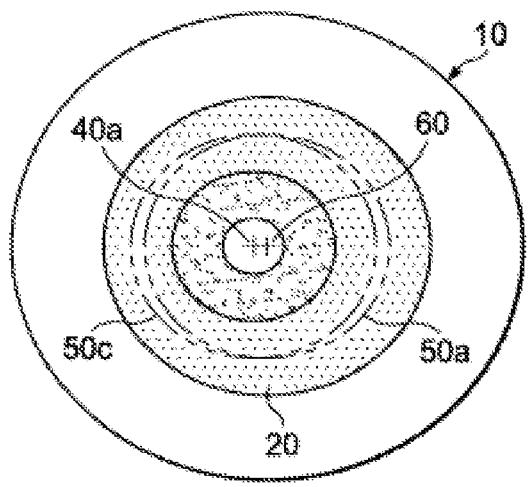
FIG. 1D is a schematic diagram of the corneal vortex of an eye and marks to indicate the corneal vortex and the pupil center of the eye of FIG. 1A, according to embodiments of the present disclosure.
Figure 1E:
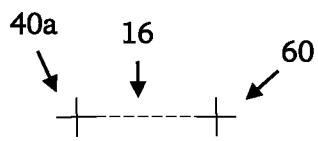
FIG. 1E is a schematic diagram of a virtual line 16 connecting the corneal vertex 60 and the pupil center 40 a at a given dilation.

Some vision correction surgeries aim to perform the surgical procedure at the corneal vertex. The corneal vertex is the intersection of the first Purkinje image of the fixation point and the optical axis of an optical examination instrument, such as a videokeratographer. The corneal vertex is the central part of the cornea, where it is usually thinner than at the corneal periphery. The corneal vertex is surrounded by the corneal periphery, which is also generally circular and extends to the edge of the cornea. The corneal vertex might be at the same location as the pupil center, but this is also often not the case. As illustrated in FIG. 1D, the corneal vertex 60 may be in a different location than any pupil center, such as pupil center 40a, such that mark 50c made on the peripheral region of cornea 20 to indicate corneal vertex 60 is not in the same location as mark 50a made to indicate pupil center 40a.

Other vision correction surgeries perform the surgery at a location other than the corneal vertex or pupil center at a given dilation. For instance, some surgeries may be performed along a virtual line 16 connecting the corneal vertex 60 and the pupil center 40 a at a given dilation.

Accordingly the disclosure includes a method of marking a cornea with a mark in preparation for vision correction surgery. First, a location for the surgical procedure is selected. The selected location may be the corneal vertex or the pupil center at a given dilation. The location may be selected based on a variety of technical factors, such as the type of vision correction surgery to be performed, the thickness of the cornea, particularly at the corneal vertex, the location of the corneal vertex with respect to the pupil center at one or more dilations, and the variation in the pupil center at different dilations. The location may also be selected based on a patient preference factor, such as whether optimal vision in bright or low light is most desirable.

Once the location has been selected, it is actually identified on the eye. First, the eye is prepared, if needed, for instance by dilating the pupil to a desired dilation. Next, an ophthalmic device is used to identify the selected location. Any ophthalmic device able to perform this function may be used, including both manual and computer-assisted devices and devices currently used in diagnostic or surgical procedures for visions correction, such as LASIK, SMILE, and cataract surgery. The device may include a microscope or other magnification lens. If the device is computer-assisted, it may include a digital image sensor, such as a photodiode array, that captures light reflected from the eye to create a digital image. A computer-assisted device may also include a processing resource programmed with an algorithm that locates the pupil center or corneal vertex. For instance, the algorithm may identify where the pupil is bounded by the iris using color detection or circle detection algorithms. It may then approximate the iris with one or more ellipses or circles and locate the centers of those ellipses or circles, which are identified as the pupil center at that dilation. When detecting the corneal vertex, a computer-assisted device may use visible, infrared, or other light and a sensor to detect the light. The device may be programmed with an algorithm to convert levels of or changes in the light to pupil centroid changes, relative to the corneal vertex and to select or mark the selected location according to surgeon's or other input, for the later surgical procedure.

Using any of the above procedures and devices, the selected location may be a point, or an area of defined shape and size, such as a circle with a defined diameter.

After identifying the selected location, a mark is made on the corneal periphery that can be used to later re-identify the selected location. The mark may be made anywhere on the corneal periphery, but typically will be at least 8 mm from the approximate corneal vertex to avoid inner parts of the cornea, which are thinner and may need to pass light. The mark may also be no more than 11 mm from the approximate corneal vertex to avoid damaging the outer regions of the cornea where it attaches to the sclera or the sclera itself.

The mark may be of any shape or size sufficient to allow later re-identification of the selected location even if the cornea is deformed. For instance, the mark may be a circle with the selected location at its center, or a plurality of sub-marks, such as lines or dots. Typically, if the mark is a plurality of sub-marks, there will be at least three such sub-marks to allow triangulation of the selected location.

The mark may be visible to the naked eye or at magnifications used in vision correction surgery, or it may be detectable only with computer assistance.

The mark may reside on the surface of the cornea, or it may penetrate the cornea. In either instance, it is designed to persist as long as needed until and during the surgery, but it may also be designed to later disappear or heal. For instance, the mark may include a biocompatible dye or may simply be a small incision The mark may be made using any suitable instrument, such as a ring marker, a laser, or a small needle, or a scalpel.

The mark may be made by hand by a surgeon, such as a surgeon using a ring marker, or it may be made by a surgeon using a computer-assisted device or by a computer-assisted device itself. Use of a computer-assisted device to both identify the selected location and make the mark may lead to more accurate mark placement.

After the mark has been made, a surgeon conducts the vision correction surgery. During the surgery, the cornea is deformed such that if the pupil center or corneal vertex were located during the surgery, it would not accurately reflect the location in the undeformed cornea. For instance, at least one corneal suction or applanation device may be applied to the cornea during surgery, causing it to deform.

Despite the conical deformation, the surgeon uses the mark to re-identify the selected location and to perform the surgical procedure at that location. The surgeon may locate the mark using the naked eye or a surgical microscope and may mentally determine the selected location. However, it is typically more accurate for the surgeon to use a computer-assisted device to locate the mark and determine the selected location. For instance, the computer-assisted device may contain a digital image sensor, such as a photodiode array, that captures light reflected from the eye to create a digital image. The computer-assisted device may be programmed with an algorithm that analyzes the digital image to locate the mark and that further re-identifies the selected location using the mark. The computer-assisted device may then convey information about the selected location to the surgeon, for instance by overlaying it on a visual display or by using sound or other indicators to inform the surgeon when an instrument is in position at the selected location. The computer-assisted device may on its own or through communication with another computer-assisted device, also position surgical equipment for performing the surgical procedure, such as a laser, forceps, or scalpel, at the selected location. The computer-assisted device may even perform the surgical procedure at the selected location.

If a surgical microscope or computer-assisted device is used to both mark the cornea and to re-identify the selected location, the same device may be used to both procedures. The same device may also be use to automatically mark the cornea, to perform the surgical procedure, or both. The use of a single device may reduce the risk of infection or physical injury that might occur if the patient moves. It may also make the entire procedure shorter.

Figure 2:
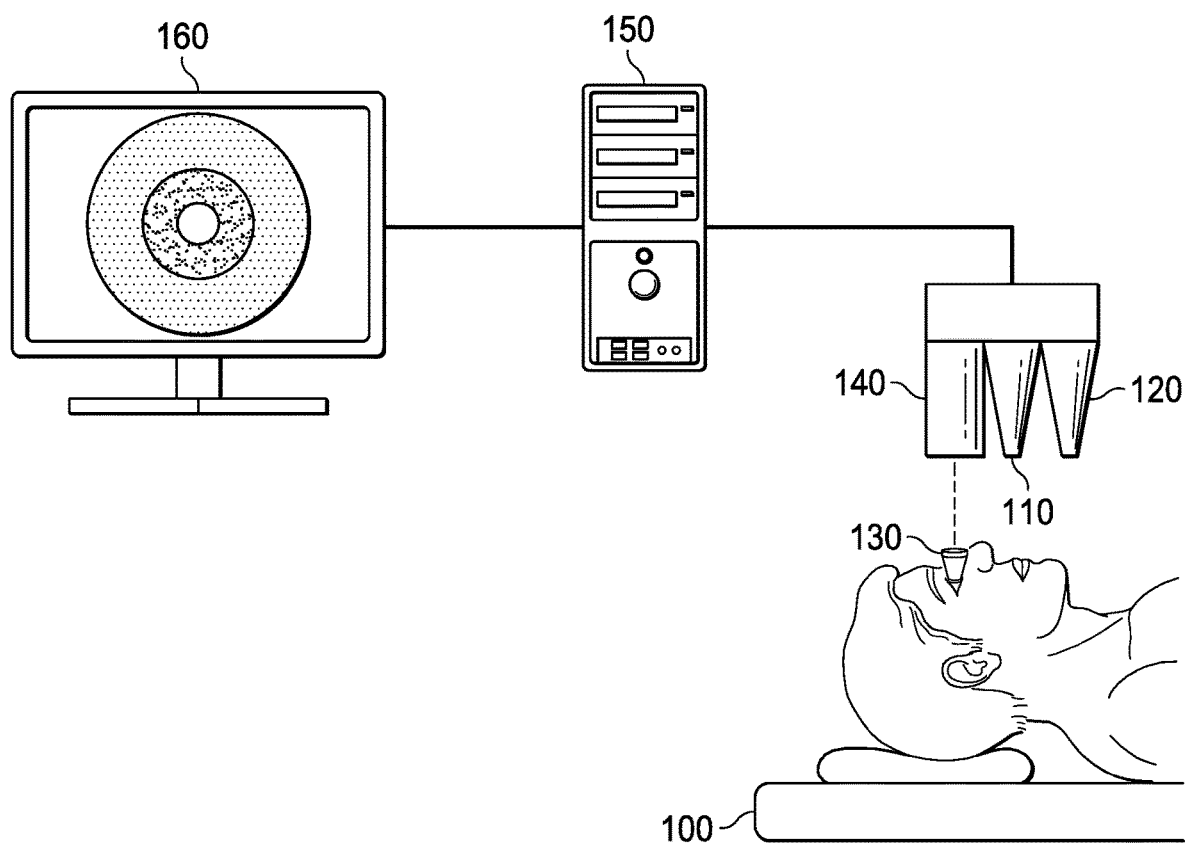
FIG. 2 is a schematic diagram of a system for performing vision correction surgery, according to an embodiment of the present disclosure.

In an example embodiment, which may be combined with any of the other features described above, a system and method for a LASIK or SMILE surgery are provided. The LASIK or SMILE system as illustrated in FIG. 2 includes a platform 100 upon which the patient rests during the surgery. It further includes femtosecond laser 110, excimer laser 120 (for a LASIK system) corneal suction device 130, which may include an applanation device such as an applanation cone, surgical digital microscope 140, computer 150, and display 160.

To conduct the LASIK or SMILE surgery, the patient is positioned on platform 100 with the patient's eye under surgical microscope 140. Surgical digital microscope 140 contains a magnifying lens and a sensor which together produce a magnified digital image of the eye on display 160. The patient's eye has been previously dilated to a selected dilation or is then dilated to the selected dilation, either of which is confirmed visually by the surgeon. The surgeon then instructs computer 150 to execute an algorithm to locate the pupil center or the corneal vertex, whichever is the selected location. A visual overlay of the selected location and the proposed mark location is displayed on the image of the eye on display 160. The surgeon confirms that the selected location appears to be accurate. Next, femtosecond laser 110 is activated to produce a plurality of, including at least three, sub-marks at the mark location. These sub-marks are small incisions in the corneal periphery approximately 8 mm to 11 mm from the center of the cornea. The sub-marks are not visually detectable by the surgeon, but are detectable by the computer using an algorithm that detects changes in the light reflected from the cornea at these sub-markings. Next, computer 150 runs another algorithm on the digital image of the eye to detect the sub-marks, and an algorithm to re-identify the selected location based on the sub-marks. Computer 150 confirms that the re-identified selected location corresponds to the selected location. If it does not, the surgeon is notified that an error has occurred while making the mark, and the procedure may be postponed until the sub-marks have healed, or new sub-marks may be made at different locations. If the re-identified selected location corresponds to the selected location, a visual overlay of both is displayed on the image of the eye on display 160 so that the correspondence may be visually confirmed by the surgeon.

Next, corneal suction device 130 is applied to the eye. This device holds the eye in place, but it also deforms the cornea. Typically it causes applanation of the cornea. Computer 150 runs an algorithm on the digital image of the eye to detect the sub-marks and an algorithm to re-identify the selected location based on the sub-marks. A visual overlay of the re-identified selected location is displayed on the image of the eye on display 160 so that the surgeon may confirm that it appears to be accurate.

If the procedure is a LASIK procedure, the surgeon then directs computer 150 to use femtosecond laser 110 to form a flap in the cornea which is approximately centered on the selected location. The surgeon then lifts this flap and directs computer 150 to use excimer laser 120 to perform the surgical procedure and ablate corneal tissue in the selected location. This ablation may be standard ablation, wavefront-sensor-guided ablation, or another form of computer-assisted ablation. After ablation, computer 150 may run another algorithm to detect whether ablation was performed properly, including whether it occurred in the selected location, which may be re-identified, if needed, using the mark.

After any washing and confirmation that the procedure has been performed correctly, the flap may be lowered and corneal suction device 130 may be removed. Computer 150 may then run another algorithm to re-identify the selected region on undeformed the eye using the mark and to confirm that ablation occurred in the selected region.

If the procedure is a SMILE procedure, the surgeon then directs computer 150 to use femtosecond laser 110 to define an intracorneal lenticule to be removed. After definition of the lenticule, computer 150 may run another algorithm to detect that the lenticule has been formed properly, including detecting whether it has been formed in the selected location, which may be re-identified, if needed, using the mark. If the lenticule was formed properly, femtosecond laser 110 is then used to form a small (typically 2 mm or less) incision at the edge of the lenticule and the surgeon then removes the lenticule from the cornea through the small incision. After removal of the lenticule, computer 150 may run another algorithm to detect that the lenticule has been removed properly from the proper location, which may include re-identifying the selected location using the mark.

After any other confirmation that the procedure has been performed correctly, corneal suction device 130 may be removed. Computer 150 may then run another algorithm to re-identify the selected region on undeformed the eye using the mark and to confirm that the lenticule was removed from the selected region.

Computer 150 and any other computer described herein may include at least a processing resource able to run the indicated algorithms. It may also include a memory and a communications module for communicating with the ophthalmic detector and, optionally, other system components such as the display and the lasers.

Variations of the above procedure, for instance using a dye injector or a computer-controlled ring marker to make the mark, may be envisioned by one of ordinary skill in the art using the teachings herein. In addition, methods of combining the above procedure with a different vision correction surgery, such as cataract surgery, may also be envisioned by one of ordinary skill in the art using the teachings herein.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A method of performing a vision correction surgery comprising:
    identifying a selected location on a cornea of an eye along a virtual line connecting a corneal vertex and a pupil center at a given dilation;
    marking the periphery of the cornea with a mark that corresponds to the selected location, the mark used to determine proper formation of a corneal lenticule, the mark being a circle or sub-marks centered about the selected location along the virtual line connecting the corneal vertex and the pupil center, the mark made using a femtosecond laser;
    deforming the cornea;
    re-identifying the selected location on the deformed cornea by detecting light reflected from the cornea at the mark; and
    performing, by a computer, a vision correction surgical procedure at the selected location while the cornea is deformed, the vision correction surgical procedure comprising:
        forming the corneal lenticule with the femtosecond laser;
        re-identifying the selected location on the cornea after the corneal lenticule is formed and when the cornea is not deformed by detecting light reflected from the cornea at the mark; and
        determining whether the corneal lenticule was properly formed relative to the selected location when the cornea is not deformed.

2. The method of claim 1, wherein the pupil center is the pupil center of a dilated pupil.

3. The method of claim 1, wherein the pupil center is the pupil center of an undilated pupil.

4. The method of claim 1, wherein the pupil center is the pupil center of the eye at a different dilation than during the surgical procedure.

5. The method of claim 1, wherein the mark is made between 8 mm and 11 mm from the approximate corneal vertex.

6. The method of claim 1, wherein deforming the cornea comprises applanating the cornea.

7. The method of claim 1, wherein re-identifying the selected location on the deformed cornea by detecting light reflected from the cornea at the mark comprises locating the mark, then determining the selected location with respect to the mark.

8. The method of claim 1, wherein the vision correction surgical procedure comprises removing a lenticule of the cornea at the selected location.

9. The method of claim 8, wherein the vision correction surgical procedure comprises:
    re-identifying the selected location on the deformed cornea by detecting light reflected from the cornea at the mark; and
    determining whether the corneal lenticule was properly removed relative to the selected location.

10. A system for vision correction surgery comprising:
    an ophthalmic detector operable to identify a selected location on a cornea of an eye along a virtual line connecting a corneal vertex and a pupil center at a given dilation;
    a marker operable to mark the periphery of the cornea with a mark that corresponds to the selected location, the mark used to determine proper formation of a corneal lenticule, the mark being a circle or sub-marks centered about the selected location along the virtual line connecting the corneal vertex and the pupil center, the mark made using a femtosecond laser;
    a corneal suction or applanation device operable to deform the cornea;
    a surgical procedure device operable to perform a vision correction surgical procedure at the selected location while the cornea is deformed; and
    a computer programmed to:
        identify the selected location;
        re-identify the selected location according to light reflected from the cornea at the mark, using information provided by the ophthalmic detector;
        use the femtosecond laser to form the corneal lenticule;
        re-identify the selected location on the cornea after the corneal lenticule is formed and when the cornea is not deformed according to the light reflected from the cornea at the mark; and
        determine whether the corneal lenticule was properly formed relative to the selected location when the cornea is not deformed.

11. The system of claim 10, wherein the surgical procedure device comprises the femtosecond laser.

12. The system of claim 10, wherein the pupil center is the pupil center of a dilated pupil or an undilated pupil of the eye.

13. The system of claim 12, wherein the pupil center is the pupil center of the eye at a different dilation than during the surgical procedure.

14. The system of claim 10, wherein the mark is made between 8 mm and 11 mm from the approximate corneal vertex.

15. The system of claim 10, wherein the algorithm is configured to re-identify the selected location by locating the mark, then determining the selected location with respect to the mark.

16. The system of claim 10, wherein the vision correction surgical procedure comprises removing the corneal lenticule at the selected location.

17. The system of claim 16, wherein the computer is programmed to:
- re-identify the selected location on the deformed cornea by detecting light reflected from the cornea at the mark; and
- determine whether the corneal lenticule was properly removed relative to the selected location.

\* \* \* \* \*